United States Patent [19]

Yeung et al.

[11] Patent Number: 4,726,818
[45] Date of Patent: Feb. 23, 1988

[54] BULK REMOVAL OF WATER FROM ORGANIC LIQUIDS

[75] Inventors: Thomas W. Yeung, Mahopac; Harvey M. Malino, South Salem, both of N.Y.

[73] Assignee: Union Carbide Corporation, Danbury, Conn.

[21] Appl. No.: 684,141

[22] Filed: Dec. 20, 1984

[51] Int. Cl.⁴ .................. B01D 53/04; B01D 53/26
[52] U.S. Cl. ................................. 55/33; 55/62; 55/75; 210/689
[58] Field of Search ............... 55/31, 33, 35, 62, 75; 210/689

[56] References Cited

U.S. PATENT DOCUMENTS

| | | | |
|---|---|---|---|
| 1,985,205 | 12/1934 | Derr | 210/689 X |
| 2,137,605 | 11/1938 | Derr | 210/689 X |
| 2,323,524 | 7/1943 | Downs, Jr. | 210/689 X |
| 3,122,486 | 2/1964 | Skarstrom | 55/62 X |
| 3,192,687 | 7/1965 | Silva et al. | 55/33 |
| 3,241,294 | 3/1966 | Walker et al. | 55/33 X |
| 3,378,992 | 4/1968 | Pierce et al. | 55/62 |
| 3,398,208 | 8/1968 | Ward | 210/689 X |
| 3,405,507 | 10/1968 | Spencer et al. | 55/62 |
| 3,712,027 | 1/1973 | Hasz | 55/33 |
| 4,030,896 | 6/1977 | Wimber et al. | 55/62 X |
| 4,273,621 | 6/1981 | Fornoff | 55/33 X |
| 4,351,732 | 9/1982 | Psaras et al. | 210/689 |
| 4,372,857 | 2/1983 | Matthews et al. | 210/689 X |
| 4,373,935 | 2/1983 | Ausikaitis et al. | 210/689 X |
| 4,385,994 | 5/1983 | Wilson et al. | 210/689 |
| 4,405,343 | 9/1983 | Othmer | 55/33 X |
| 4,407,662 | 10/1983 | Ginder | 55/33 |
| 4,421,651 | 12/1983 | Burkholder et al. | 210/689 X |
| 4,460,476 | 7/1984 | McCaffrey et al. | 210/689 |
| 4,487,614 | 12/1984 | Yon | 55/33 |

Primary Examiner—Robert Spitzer
Attorney, Agent, or Firm—Richard G. Miller

[57] ABSTRACT

An improved method for the bulk drying of water-containing organic feedstocks by means of selective adsorption of the water in fixed molecular sieve beds wherein the improvement comprises integrating a series of at least four fixed adsorption beds in a manner such that at least two of the beds are always involved in the adsorption-drying phase of the process cycle, and at least two of the beds are always undergoing some portion of the regeneration phase in such a manner that a closed-loop non-condensible purge gas stream used to heat and to cool the beds undergoing regeneration is passed first through the bed being cooled and thereafter through the bed being heated, with the heat energy removed from the former being imparted to the latter.

5 Claims, 1 Drawing Figure

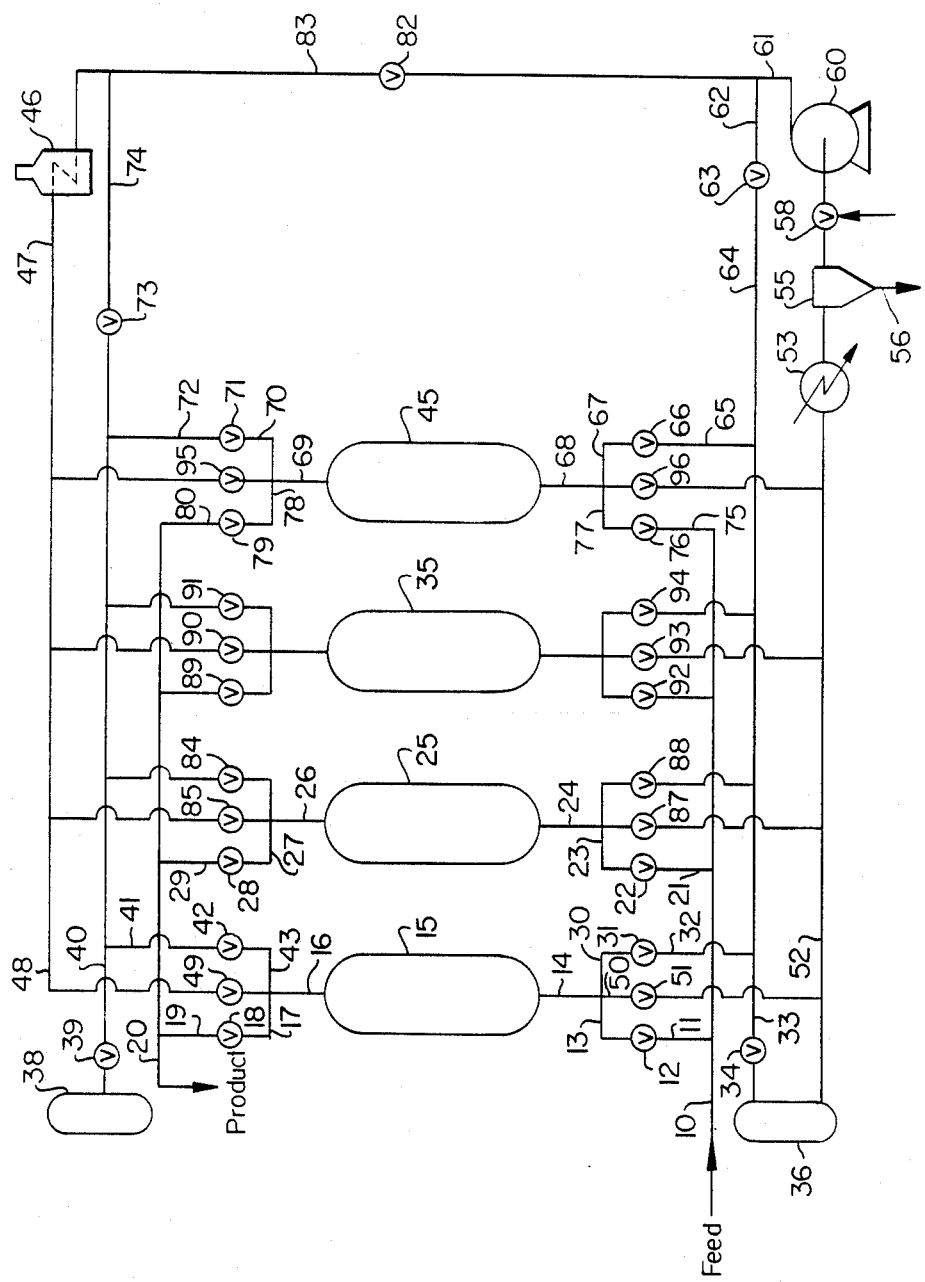

BULK REMOVAL OF WATER FROM ORGANIC LIQUIDS

FIELD OF THE INVENTION

The present invention relates in general to the bulk separation of water from miscible mixtures thereof with organic liquids, and more particularly to the dehydration of organic liquids such as ethanol by means of selectively adsorbing the water constituent on molecular sieve adsorbents during passage of the water-containing mixture in the liquid phase through a fixed adsorbent bed of a multiple-bed adsorption-purification system.

BACKGROUND

Until recently, the drying of fluids, either gases or liquids, by the selective adsorption of the water constituent was economically feasible only when the concentration of water in the fluid was small, i.e., present at a level of a few parts per million up to about 2.5 weight percent. For higher water-content feedstocks which were normally in the vapor phase, refrigeration processes were usually resorted to. In the case of high water-content normally liquid feedstocks, distillation procedures were most commonly employed. A principal difficulty encountered in attempted vapor phase processes was the phenomenon known as "crossover" in which the heat of adsorption of the water vapor within the adsorbent bed creates a heat front which remains within or behind the water mass transfer front as the two fronts advance along the bed. This resulted in a reduced efficiency of the adsorbent for water removal by the lowering of the effective water equilibrium capacity and the elongation of the mass-transfer front with ensuing early breakthrough of water into the product stream. In liquid phase processes, relatively short adsorption-regeneration cycles were mandated by the rapid exhaustion of the water-adsorption capacity of a fresh adsorption bed due to the high concentrations of water present in the feedstock. It was found, however, that it was extremely difficult to transport the high molar density liquid within the adsorption system during the regeneration and bed-filling stages of the cycle quickly enough to meet the demands of the imposed short cycle. In both types of processes, a major obstacle to commercialization was the lack of an economical bed regeneration procedure.

In U.S. Pat. No. 4,373,935 issued Feb. 15, 1983 to Ausikaitis et al. a method for successfully operating a vapor-phase bulk drying process for treating high water content feedstocks is described. In this process the inefficiency inherent in the unavoidable non-isothermal adsorption step caused by the crossover phenomenon is found to be overbalanced by utilizing the heat energy generated during adsorption to create a more efficient thermal regeneration step.

In the case of liquid phase operation, however, no significant breakthrough in devising a suitably economical bulk-drying process has been proposed in the prior art.

SUMMARY OF THE INVENTION

The present invention comprises a novel liquid-phase adsorption process for the bulk drying of organic materials utilizing an adsorption system having at least four fixed adsorption beds containing molecular sieve adsorbent. In the operation of the process the four beds of the adsorption system are integrated in a manner such that at all times at least two of the beds are involved in treating the water-containing feedstock to selectively adsorb water therefrom and produce an organic product effluent of the desired degree of dryness, and at least two of the beds are undergoing some step of a regenerative procedure comprising the sequence of (a) draining, (b) heating, (c) cooling and (d) filling, the sequence of the steps of the regenerative procedure in the two beds being regulated so that the cooling step in one bed occurs substantially within the period the other bed is undergoing the heating step. This permits the use of a single non-condensible purge gas stream to accomplish both the cooling and heating steps in the respective beds by means of a closed-loop flow cycle which transfers the heat energy from the bed being cooled to the bed being heated with a consequent very substantial economic advantage in energy requirements. Perhaps an even greater economic benefit is achieved by the saving in capital investment in the construction of a commercial-scale system used to carry out the present process. Whereas two separate regeneration units are required for the operation of two dual bed adsorption systems, in the present process the integrated four bed system requires but a single regeneration unit.

DETAILED DESCRIPTION OF THE INVENTION

The feedstocks suitably treated by the processes of this invention are any mixtures of water with one or more organic compounds which contain at least 2.5 weight percent water and which can be maintained in the liquid phase under the adsorption temperature and pressure conditions imposed. Preferred feedstocks are those which cannot be dried by conventional distillation techniques, i.e., are either aqueous azeotropes or can form azeotropic mixtures by appropriate changes in the relative proportions of their constituents. Such mixtures include those wherein the organic constituent is ethanol, isopropanol, sec-butanol, tert-butanol, allyl alcohol, benzene, toluene, diethyl ether, diisopropyl ether, ethylene chloride, n-propyl formate, ethyl acetate, methyl propionate, ethyl isobutyrate, n-propyl nitrate, methyl tertiary butyl ether, methyl ethyl ketone, formic acid and pyridine. Particularly preferred feedstocks are mixtures of one or more primary alcohols, having from 2 to 5 carbon atoms inclusive, with water in which the water content is from 2.5 to about 20 weight percent. An especially preferred feedstock is an ethanol-water mixture containing from about 5.0 to 10 volume percent (7.6 to 14.3 weight percent) water.

The temperature and pressure conditions for the adsorption step are selected so as to maintain the feedstock in the liquid phase. It is preferred that the feedstock, in addition to being below the critical temperature of its organic constituent, be within the range of about 15° C. to 40° C. and at an appropriate corresponding pressure within the range of about 1 atmosphere (absolute) up to about 100 psia. During the purge desorption (heating) step of the bed regeneration procedure, the temperature of the non-condensible purge, at the time it enters an adsorbent bed during the heating step, is preferably from about 175° C. to 235° C., and at the time it enters an adsorbent bed during the cool-down step is at any temperature low enough to reduce the bed temperature sufficiently to carry out the subsequent adsorption step under the conditions set forth above. The adsorption-regeneration cycle is preferably isobaric or nearly isobaric, i.e., the desorption step should be essentially of the thermal-swing rather than the pressure-swing type.

The non-condensible purge gas used in the bed regeneration portion of the cycle is any substance in the vapor phase and which under the imposed conditions of the process, is not harmful to the adsorbent mass, does not appreciably react with the feedstock constituents, is not strongly adsorbed by the adsorbent and is readily separable from admixture with water vapor and vapors of the organic constituent of the feedstock by reduced-temperature condensation of those last named substances. Preferably the non-condensible purge gas is one, or a mixture of two or more, of nitrogen, hydrogen, helium, carbon dioxide or methane.

The molecular sieve adsorbent employed is not a narrowly critical factor. The well-known crystalline zeolite molecular sieves are well suited to use in the process, but other crystalline microporous materials, which have more recently become available, such as the aluminophosphates disclosed in U.S. Pat. No. 4,310,440 and the silicoaluminophosphates disclosed in U.S. Pat. No. 4,440,871, are also advantageously utilized. In all events, however, the particular adsorbent employed should exhibit a marked preference for the adsorption of water molecules with respect to the other (organic) constituents of the feedstock. A hydrophilic molecular sieve having pore diameters small enough to exclude most of the molecular species of the feedstock based on molecular size considerations, such as zeolite 3A (the potassium cationic form of zeolite A) is particularly preferred. A comprehensive listing of both synthetic and naturally occurring zeolites is set forth in "Zeolite Molecular Sieves" by D. W. Breck, John Wiley and Sons, New York (1974). For most feedstocks, including those in which the organic constituent is ethanol of a higher alcohol, small pore mordenite, particularly the mineral form such as commercially available under the Union Carbide Corporation designation AW-300, is highly effective as an adsorbent in the present process and is a preferred adsorbent for use therein.

As used herein in this specification and in the appended claims, the following terms shall have the meanings set forth below: "Adsorption" means that step of the present process wherein feedstock is passed into an adsorption bed in which the bed void space, i.e., the space in the bed which can be occupied by feedstock molecules other than the intra-crystalline pore system of the molecular sieve adsorbent, is substantially occupied by feedstock constituents, and whereby water is selectively adsorbed by the molecular sieve adsorbent and a water-depleted organic product is recovered as an effluent stream.

"Drain" means that step immediately following the adsorption step in a particular bed in which the major proportion of the feedstock occupying the bed void space is withdrawn from the bed, usually by gravity flow with the aid of some purge gas, and preferably in a direction counter-current to the direction of flow of feedstock into the bed during the adsorption step.

"Heating" means that step immediately following the drain step in a particular bed in which heated non-condensible purge gas is passed through the bed in a direction preferably counter-current to the direction of flow during the adsorption step whereby the temperature of the adsorbent is increased and adsorbed water molecules become desorbed and are carried out of the bed as a part of the purge gas effluent. By virtue of this step, the adsorption capacity of the adsorbent is restored for a subsequent adsorption-dehydration step.

"Stand-by" means a period of the process cycle in which a particular bed is not actively engaged in any of the other steps described herein. This inactive step is not essential in the present process, but can be advantageously employed to facilitate the necessary commencement of the cooling step in one of the beds not undergoing adsorption at essentially the same time as the heating step is begun in another bed of the process system. This matter is explained further by reference to the description of the working example appearing below.

"Cooling" means the step of the present process wherein an adsorption bed which has undergone the heating step described above and is consequently at a temperature substantially above that desired for carrying out an adsorption step therein, is reduced in temperature by the passage therethrough, preferably in a direction co-current to the direction of the flow during the adsorption step, of a cooler non-condensible gas stream whereby heat energy is carried out of the bed and the temperature of the adsorbent mass is decreased.

"Filling" is essentially the same as the adsorption step except that the feedstock enters an adsorption bed in which the bed void space is occupied by non-condensible purge gas rather than feedstock liquid and essentially all of the adsorbent is in an activated state. Accordingly filling can be accomplished using a more rapid rate of introduction of feedstock.

DRAWINGS

The sole FIGURE of the drawings is a schematic flow diagram showing a four-bed adsorption system suitable for the practice of a preferred embodiment of the present invention.

The present invention is exemplified and illustrated by the following description made with reference to the flow diagram of the drawing: The adsorption system consists of four adsorbent beds, Nos. 15, 25, 35, and 45 respectively, each containing essentially the same quantity of zeolite 3A adsorbent particles. The feedstock being treated to reduce its water content is a water-ethanol mixture containing 7.6 wt.% water (190 proof alcohol). The product is ethanol containing less than 0.8 wt. % water (199 proof). The feedstock enters the system through line 10 at a pre-determined rate commensurate with the size of the adsorption beds. In this particular embodiment, the system is designed such that each of the four beds undergoes a twelve-hour adsorption period and a twelve-hour regeneration period to complete one full cycle. The twelve-hour regeneration procedure consists of a one-hour draining step, a five-hour heating step, one hour on standby, a one and one-half hour cooling step and a filling step which occupies a three and one-half hour period. The integrated cycles of the four beds is shown graphically below:

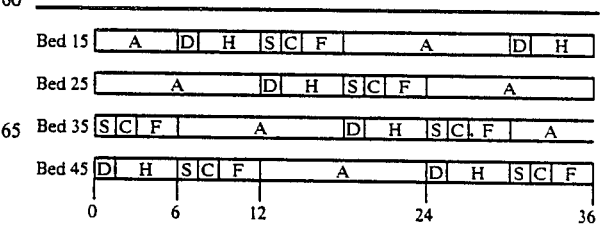

-continued

Time, Hr. ⟶

| | Time, Hr. |
|---|---|
| A = Adsorption | H = Heating |
| D = Drain | C = Cooling |
| S = Standby | F = Filling |

At the starting point of the present process description, bed 15 and bed 25 are operating in the adsorption phase of the cycle, and beds 35 and 45 are undergoing some step of the regeneration phase of the cycle. Bed 15 is six hours into its adsorption step and bed 25 is just beginning its twelve-hour adsorption step. Feedstock from line 10 passes through line 11, valve 12, line 13 and line 14 into bed 15 wherein the water content is substantially adsorbed and the dehydrated product ethanol leaves the bed through line 16, line 17, valve 18, and line 19 and is removed from the system through line 20. In the case of bed 25, a portion of the incoming feedstock through line 10 is passed through line 21, valve 22 and lines 23 and 24 into bed 25 during the adsorption step therein, and purified product is recovered as the effluent through lines 26 and 27, valve 28, and line 29, and is removed from the system through line 20. Six hours after the starting point of this description the adsorption step in bed 15 is terminated and the regeneration portion of the overall process cycle is begun by draining therefrom the feedstock held in the bed void space. This is accomplished by permitting the void space liquid to drain from bed 15 through line 14, line 30, valve 31, lines 32 and 33, valve 34 to holding tank 36. The liquid in the bed void space is replaced with nitrogen contained in recapture tank 38 which passes through valve 39, lines 40 and 41, valve 42 and lines 43 and 16 into bed 15. This draining step requires about one hour. With reference to the graphic representation of the integrated cycles of the four beds 15, 25, 35 and 45 shown above, it can be seen that while bed 15 is being drained, beds 25 and 35 are both on an adsorption step and bed 45 is on standby. This standby period permits bed 15 to begin its heating step at the same time the cooling step in bed 45. It can also be observed that at the time any of the beds begins a cooling step another bed begins a heating step and the remaining two beds are already into the adsorption steps. The integration of the cooling and heating steps is a novel feature of the present process and is illustrated with reference to beds 15 and 45. By the appropriate setting of valves, a closed loop is established within the system as follows, starting with heater 46. The fluid flowing in the closed loop at the time it enters heater 46 is principally nitrogen with minor proportions of water vapor and ethanol vapor, whose presence is explained hereinafter. From heater 46, wherein it is heated to 175° to 235° C., the nitrogen gas stream flows through line 47, line 48, valve 49 and line 16 into bed 15. During the passage through bed 15, the nitrogen stream heats the adsorbent therein and desorbs the water removed from the feedstock during the previous adsorption step therein. At the same time the nitrogen stream is cooled substantially and flows out of bed 15 laden with water vapor through line 14, line 50, valve 51 and line 52 to cooler-condenser 53 wherein the temperature is further lowered to condense out a substantial amount of the water vapor and ethanol vapor which is present. From the condenser 53 the nitrogen gas stream passes to knock-out 55 wherein the liquid water-ethanol mix is removed from the system through line 56. The vapor phase then passes through valve 58 to compressor 60, and thence through lines 61 and 62, valve 63, lines 64 and 65, valve 66 and lines 67 and 68 into bed 45. Just prior to receiving this cool nitrogen stream through line 68, bed 45 has undergone the heating step and is on standby. As the nitrogen stream passes co-currently through bed 45 it picks up heat energy from the adsorbent mass therein and carries it out through lines 69 and 70, valve 71, line 72, valve 73 and line 74 to heater 46. Thus on its passage through heater 46, the nitrogen purge gas stream being fed to heat bed 15 need only be further heated by an amount equivalent to the heat loses occurring through the walls of the process system. After about a period of 1.5 hours, bed 45 is sufficiently cooled to be ready to be filled with feedstock and thereafter to begin an adsorption step. For purposes of filling bed 45, the void space liquid from bed 15 which has previously been drained into holding tank 36 is utilized, thereby avoiding the need to alter the carefully regulated flow rate of the fresh feedstock entering the system through line 10. The liquid from tank 36 is passed through valve 34, lines 33 and 65, valve 66, lines 67 and 68 into bed 45. After filling is complete, a portion of the feedstock through lines 10 and 75, valve 76 and lines 77 and 68 is passed into bed 45, and the product effluent passes through lines 69, and 78, valve 79, line 80 and leaves the system through line 20. Meanwhile the heating of bed 15 continues by removing the portion of the closed loop which previously passed through bed 45 while that bed was being cooled. This is readily accomplished by closing valve 63 and valve 73 and passing the nitrogen stream through compressor 60, through line 61 and valve 82 and line 83 to heater 46, and thence through line 47, line 48 valve 49 and line 16 to bed 15. By the foregoing described procedures each of the beds of the system undergoes adsorption, draining, standby, heating, cooling the filling as shown graphically above.

The four bed adsorption system described above is readily automated. The following table indicates the valve sequencing schedule which is employed. Valve 58 is a control valve used to adjust the nitrogen purge gas make-up in the regeneration loop.

| Bed 15 | A | | D | H | | S | C | F | | A | | |
| Bed 25 | | A | | | | D | H | | S | C | F | |
| Bed 35 | S | C | F | | | A | | | | D | H | |
| Bed 45 | D | H | | S | C | F | | | A | | | |

| STEP | I | II | III | IV | V | VI | VII | VIII | IX | X | XI | XII |
|---|---|---|---|---|---|---|---|---|---|---|---|---|
| V-18 | O | O | O | X | X | X | X | X | X | O | O | O |
| V-49 | X | X | X | X | O | O | X | X | X | X | X | X |
| V-42 | X | X | X | O | X | X | X | O | O | X | X | X |
| V-12 | O | O | O | X | X | X | X | X | X | O | O | O |
| V-51 | X | X | X | O | O | O | X | X | X | X | X | X |
| V-31 | X | X | X | O | X | X | O | O | X | X | X | X |
| V-28 | O | O | O | O | O | O | X | X | X | X | X | X |
| V-85 | X | X | X | X | X | X | O | O | X | X | X | X |
| V-84 | X | X | X | X | X | O | X | X | X | X | O | O |
| V-22 | O | O | O | O | O | O | X | X | X | X | X | X |
| V-87 | X | X | X | X | X | X | O | O | X | X | X | X |
| V-88 | X | X | X | X | X | O | X | X | X | O | O | O |
| V-89 | X | X | X | O | O | O | O | O | O | X | X | X |
| V-90 | X | X | X | X | X | O | O | O | X | X | O | O |
| V-91 | X | O | O | X | X | X | X | X | O | X | O | X |
| V-92 | X | X | X | O | O | O | O | O | O | X | X· | X |
| V-93 | X | X | X | X | X | X | O | O | X | X | O | O |
| V-94 | X | O | O | X | X | X | X | X | X | O | X | O |
| V-79 | X | X | X | X | X | O | O | O | O | O | O | O |
| V-95 | X | O | O | X | X | X | X | X | X | X | X | X |

-continued

```
Bed 15 [    A    |D|  H  |S|C|  F  |    A    ]
Bed 25 [         A         |D|  H  |S|C|  F  ]
Bed 35 [S|C|  F  |         A         |D|  H  ]
Bed 45 [D|  H  |S|C|  F  |         A         ]
```

| STEP | I | II | III | IV | V | VI | VII | VIII | IX | X | XI | XII |
|---|---|---|---|---|---|---|---|---|---|---|---|---|
| V-71 | O | X | X | X | O | O | X | X | X | X | X | X |
| V-76 | X | X | X | X | X | O | O | O | O | O | O | O |
| V-96 | X | O | O | X | X | X | X | X | X | X | X | X |
| V-66 | O | X | X | X | O | O | X | X | X | X | X | X |
| V-58 | X | O | O | X | O | O | X | O | O | X | O | O |
| V-82 | X | X | O | X | X | O | X | X | O | X | X | O |
| V-73 | X | O | X | X | O | X | X | O | X | X | O | X |
| V-39 | O | X | O | O | X | O | O | X | O | O | X | O |
| V-34 | O | X | O | O | X | O | O | X | O | O | X | O |
| V-63 | X | O | X | X | O | X | X | O | X | X | O | X |

"X" = valve closed
"O" = valve opened
"V" = valve

What is claimed is:

1. The process for bulk drying of organic feedstocks containing at least 2.5 weight percent water by passage thereof through a fixed bed of a molecular sieve adsorbent whereby the water is selectively adsorbed and the dehydrated organic material is recovered as the bed effluent, the improvement which comprises:

providing an adsorption system comprising at least four fixed adsorption beds, said adsorption beds being integrated in a manner such that at all times at least two of the said beds are involved in treating the water-containing feedstock to selectively adsorb water therefrom and produce an organic product effluent of the desired degree of dryness, and at least a first bed and a second bed of the said beds are undergoing some step of a regenerative procedure comprising the sequence of (a) draining, (b) heating (c) cooling and (d) filling, the sequence of the steps of the regenerative procedure being regulated so that the cooling step in said first bed occurs substantially within the period said second bed involved in said regenerative procedure is undergoing the heating step, said regenerative procedure being accomplished by means of a non-condensable purge gas stream passing through a closed-loop in such a manner than the non-condensable purge gas stream passing through the said first bed being cooled is also passing through the said second bed being heated whereby at least a portion of the heat energy being removed from the said first bed being cooled is being imparted to the said second bed being heated.

2. Process according to claim 1 wherein the sequence of the steps of the regenerative procedure includes a standby step, and the sequence is regulated so that the cooling step in a first bed occurs substantially within the period said second bed in said regenerative procedure is undergoing the heating step and also the standby step period in a third bed occurs simultaneously with the drain period in a fourth bed.

3. Process according to the claim 1 or claim 2 wherein the adsorption system provided contains four fixed adsorption beds.

4. Process according to claim 1 or claim 2 wherein the organic feedstock being dried is a mixture which is an aqueous azeotrope or a mixture which can form an azeotrope.

5. Process according to claim 1 or claim 2 wherein the organic feedstock is a mixture of water and one or more primary alcohols having from 2 to 5 carbon atoms inclusive wherein the water content is from 2.5 to 20 weight percent.

* * * * *